United States Patent
Scheiblich et al.

(10) Patent No.: US 6,376,426 B1
(45) Date of Patent: Apr. 23, 2002

(54) HERBICIDAL 3-(HETEROCYCL-1-YL)-URACILS

(75) Inventors: Stefan Scheiblich, Mainz; Trevor Newton, Schwabenheim; Peter Johannes Servaas Savio van Eijk, Ingelheim; Isabel Waldeck, Gensingen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/495,322

(22) Filed: Jan. 31, 2000

Related U.S. Application Data

(63) Continuation-in-part of application No. 09/298,019, filed on Apr. 23, 1999, now abandoned.

(51) Int. Cl.$^7$ .................. C07D 239/54; A01N 43/54
(52) U.S. Cl. ....................... 504/136; 544/310
(58) Field of Search ............ 544/310; 504/136

(56) References Cited

U.S. PATENT DOCUMENTS 3,397,050 A   8/1968   Loux ................... 544/310

FOREIGN PATENT DOCUMENTS

| JP | A-91 287 585 | 12/1991 |
| JP | A-93 202 031 | 8/1993 |
| WO | WO 94/04511 | 3/1994 |
| WO | WO 98/27082 | 6/1998 |
| WO | WO 98/27088 | 6/1998 |
| WO | WO 98/34924 | 8/1998 |

*Primary Examiner*—Richard L. Raymond
*Assistant Examiner*—Venkataraman Balasubramanian
(74) *Attorney, Agent, or Firm*—Barbara V. Maurer

(57) ABSTRACT

The invention relates to novel 3-heterocycl-1-yluracils of formula I:

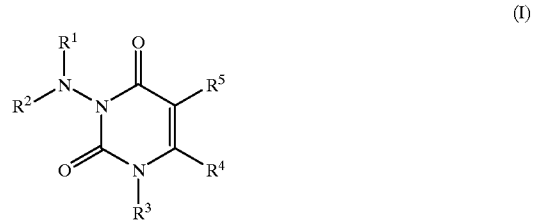

wherein $R^1$ and $R^2$ together with the interjacent nitrogen atom form an optionally substituted, optionally benzo-condensed 5-membered heterocyclic ring and $R^3$ through $R^5$ have the meaning given in claim 1. The invention also relates to a method of the production of these substances and to herbicidal compositions containing such compounds as active ingredients.

13 Claims, No Drawings

HERBICIDAL 3-(HETEROCYCL-1-YL)-URACILS

This is a continuation in part of application(s) Ser. No. 09/298019 filed on Apr. 23, 1999 now abandoned, the entire disclosure of which is hereby incorporated by reference.

BACKGROUND OF THE INVENTION

The present invention relates to heterocyclyl-uracils in which the 3-position of the uracil moiety is directly attached to the nitrogen of the heterocyclyl group.

Selective herbicidal compounds play an important role in agriculture and related fields. Growers seek herbicides that kill pest plants, but do not reduce crop yield. Although numerous selective herbicides have been described, there is, nevertheless, a considerable interest in new compounds having superior or different activities, because the known herbicidal compounds either are not suitable for application in certain crops, or are not sufficiently selective or active.

Herbicidal heterocyclyl-uracils are known, for example, from JP-A 91-287 585, JP-A 93 202 031, WO 98/27082 and WO 98/27088.

However, heterocyclyl-uracils in which the heterocyclyl group is attached to the uracil group in the 3-position via the nitrogen atom have not yet been described.

SUMMARY OF THE INVENTION

The present invention provides novel 3-heterocycl-1-yluracil compounds of the formula (I)

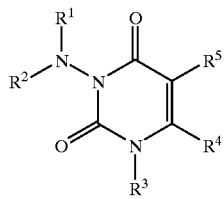

(I)

wherein
- $R^1$ and $R^2$ together with the interjacent nitrogen atom form an optionally substituted, optionally benzo-condensed 5-membered heterocyclic ring,
- $R^3$ represents a hydrogen atom, or an amino, a cyano or a hydroxy group, or an alkyl or alkoxy group optionally substituted by one or more substituents selected from halogen atoms, cyano and alkoxy groups,
- $R^4$ represents a halogen atom, or a formyl, a hydroxyiminomethyl, a cyano, a carboxy, an alkoxycarbonyl, a carbamoyl, a thiocarbamoyl, an alkyl, an alkoxy, an alkylthio, a haloalkyl, a haloalkoxy or a haloalkylthio group,
- $R^5$ represents a hydrogen or halogen atom, or an alkyl group; or an agriculturally acceptable salt or N-oxide thereof.

The new compounds show excellent selective herbicidal activity in various crops.

It is an object of the present invention to provide novel, selective herbicidal compounds.

It is also an object of the invention to provide methods for controlling undesired plant growth by contacting said plants with a herbicidally effective amount of the new compounds.

It is another object of the invention to provide selective herbicidal compositions containing the new compounds as active ingredients.

These and other objects and features of the invention will be more apparent from the detailed description set forth herein below, and from the appended claims.

DETAILED DESCRIPTION OF THE PREFERRED EMBODIMENTS

It has surprisingly been found that the compounds of the formula (I)

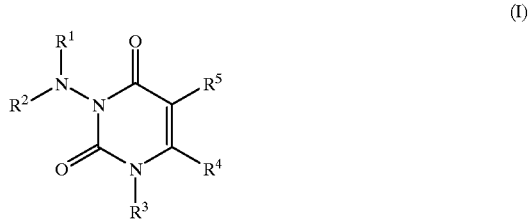

(I)

wherein
$R^1$ through $R^5$ are as described above, and the agronomically acceptable salts or N-oxides thereof, show considerable herbicidal activity and high selectivity in certain crops, such as wheat, soybeans and rice, in pre- and post-emergence applications on both broadleaf and grassy weed species.

Generally, in compounds of the present invention, alkyl, alkenyl or alkynyl groups, unless otherwise specified, may be linear or branched and may contain up to 12, preferably up to 6, and most preferably up to 4, carbon atoms. Alkyl groups preferably contain one to six carbon atoms, alkenyl and alkynyl groups contain preferably two to 8 carbon atoms. Examples of such groups are methyl, ethyl, propyl, vinyl, allyl, propargyl, isopropyl, butyl, isobutyl and tertiary-butyl groups. The alkyl portion of a haloalkyl, haloalkenyl, haloalkoxy, alkylthio, haloalkylthio or alkoxy group suitably has up to 12 carbon atoms, preferably up to 6, and most preferably up to 4, carbon atoms. The double bond of the alkenyl and haloalkenyl groups is as a rule located in the 1- or 2-position with respect to the point of their attachment. The number of carbon atoms in the alkoxyalkyl, alkoxyalkoxy or dialkoxyalkyl groups is up to 12, preferably up to 6, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine.

The term "heterocylyl" shall mean a heteroaromatic or heteroaliphatic ring containing at least one nitrogen atom. Examples include azoles such as imidazole, pyrrole, pyrazole and triazole as well as the corresponding hydrogenated groups.

The term "benzo-condensed" shall mean a bicyclic aromatic ring system, in which one ring is a benzene ring and the other is a heterocyclyl group. Examples include indole, indazol, isoindol, carbazol, benzimidazol and benzotriazol.

Haloalkyl, haloalkenyl, haloalkylthio and haloalkoxy are preferably mono-, di-, tri-, tetra- or pentafluoroalkyl, -alkenyl, -alkylthio and -alkoxy, or monochloro- or dichloroalkenyl, or monobromoalkenyl, especially preferred are trifluoromethyl, tetrafluoroethyl, pentafluoroethyl, octafluorobutyl, 3,3,3-trifluoroprop-1-enyl, 2-methyl-3,3,3-trifluoroprop-1-enyl, 4,4,4-trifluorobut-1-enyl, 1,2-difluorobuta-1,3-dienyl, 1- or 2-chlorovinyl, 2,2-dichlorovinyl, 1,2-dichlorovinyl, 1,2-dichloroprop-1-enyl, 3,3,3-trichloroprop-1-enyl, 2-bromoallyl, difluoromethoxy, trifluoromethylthio, difluoromethylthio and trifluoromethoxy.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, haloalkylthio, alkylamino and dialkylamino groups, specific examples of such substituents include phenyl, halogen atoms, nitro, cyano, hydroxyl, $C_{1-4}$-alkoxy, $C_{1-4}$-haloalkoxy, $C_{1-4}$-haloalkylthio and $C_{1-4}$-alkoxycarbonyl groups.

Also included in the invention are the stereo and optical isomers of the compounds claimed and mixtures of these isomers in all proportions.

The terms herbicide and herbicidal are used to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term herbicidally effective amount is used to denote any amount which achieves such control or modification when applied to the undesired plants themselves or the area in which these plants are growing. The term plants is intended to include germinated seeds, emerging seedlings and established vegetation, including both roots and above-ground portion.

The term agriculturally acceptable salts is used herein to denote a salt or salts which readily ionize in aqueous media and includes sodium, potassium, calcium, ammonium, and magnesium salts and acid salts such as hydrochloride, sulfate and nitrate.

The compounds according to formula I include oils, gums, or, predominantly, crystalline solid materials. They possess a high herbicidal activity within a wide concentration range can be used in agriculture or related fields for the control of undesired plants such as:

dicotyledoneous species: Abutilon, Amaranthus, Ambrosia, Anthemis, Brassica, Centaurea, Chenopodium, Chrysanthemum, Cirsium, Convolvus, Datura, Galeopsis, Galinsoga, Galium, Ipomoea, Lamium, Lepidium, Matricaria, Papaver, Pharbitis, Polygonum, Portulaca, Senecio, Sinapis, Sesbana, Solanum, Sonchus, Stellaria, Urtica, Veronica, Viola and Xantium;

monocotyledoneous species: Alopecurus, Apera, Avena, Brachiaria, Bromus, Cyperus, Digitada, Echinochloa, Eleocharis, Elymus, Fimbristylis, Ischaemum, Lolium, Monochoria, Panicum, Poa, Sagittaria, Setaria and Sorghum.

The compounds of formula I can be used in particular for the control of Alopecurus myosuroides, *Echinochloa crusgalli, Setaria viridis, Galium aparine, Stellaria media, Veronica persica, Lamium purpureum, Viola arvensis, Abutilon theophrasti, Ipomoea purpurea* and *Amaranthus retroflexus* by pre- and post-emergence application.

Some of the compounds of formula I demonstrate selective control of plant species in certain crops, such as rice, corn, wheat, barley and soybean.

Preferred compounds within the above definitions are those in which $R^3$ represents an amino, a hydroxy or a methyl group, $R^4$ represents a halogen atom, or a cyano, a $C_{1-4}$ fluoroalkyl, a $C_{1-4}$fluoroalkoxy or a $C_{1-4}$fluoroalkylthio group, $R^5$ represents a hydrogen or halogen atom, or a methyl group. Most preferred are the compounds of formula I wherein $NR^1R^2$ represents a group selected from the formulae (1) and (2)

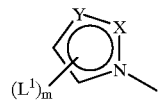

(1)

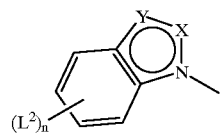

(2)

wherein

X represents N or $CR^6$,

Y represents N or $CR^7$, $R^6$ represents a hydrogen or halogen atom, or a formyl, a nitro, a alkoxyiminoalkyl, a cyano, a carboxy, an amino, an alkylamino, an alkoxycarbonyl, a carbamoyl, a thiocarbamoyl an alkyl or an alkoxy group, $R^7$ represents a hydrogen or halogen atom or an alkyl group;

$L^1$ and $L^2$ each independently represent hydrogen; halogen; nitro; amino; hydroxy; cyano; alkyl; alkoxyiminoalkyl; alkenyloxyimino-alkyl; alkenyloxyimino-alkoxycarbonyl-alkyl; alkoxycarbonyl-alkoxyiminoalkyl, hydroxy-alkyl; alkoxy-alkyl; di-(alkoxy)-alkyl, di-(alkylthio)-alkyl, alkylsulfonylamino-alkyl; haloalkylsulfonylamino-alkyl; (alkyl)$_r$ amino-alkyl; (alkylcarbonyloxy)$_z$-alkyl; haloalkyl; cyanoalkyl, cyanoalkenyl, formyl; alkylcarbonyl; or $ZR^8$ wherein Z is O, $NR^9$ or $S(O)_r$ or a single bond;

$R^8$ is —$(R^{10})_s$—$CWR^{11}$; —$(R^{10})_s$—$SO_2R^{11}$;

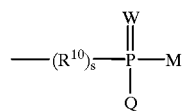

alkyl; haloalkyl; hydroxyalkyl; arylalkyl; cyanoalkyl; alkanoyloxyalkyl; alkoxyalkyl; cycloalkyl, alkenyl; alkoxyimino-alkoxycarbonyl-alkyl, di-(alkoxy)-alkyl or alkynyl;

$R^9$ is hydrogen; alkyl; alkenyl; alkynyl, amino, formyl or alkylcarbonyl;

$R^{10}$ is $NR^{12}$, alkylidene or alkenylidene or a group of formula

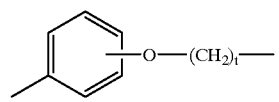

$R^{11}$ is alkyl; haloalkyl; haloalkoxy, hydrogen; hydroxy; alkoxy; alkoxyalkyl; alkanoyloxyalkyl, alkanoyloxyalkoxy, alkoxyalkoxy; alkoxyalkylamino; dialkoxyalkylamino; aryl, aryloxy; azolyl, azolyloxy, cycolalkyl, cycloalkoxy, aralkyl; aralkoxy, alkoxycarbonyl; alkoxycarbonyloxy, hydroxycarboxyl; alkoxycarbonylalkyl; alkoxycarbonylalkoxy,; hydroxycarbonylalkoxy, (alkyl)$_r$ amino; (cycloalkyl)$_r$ amino; N-cycloalkyl-N-(alkyl)$_s$ amino; (alkyl)$_r$ hydrazino; alkoxycarbonyl-alkylamino; hydroxyalkylamino; (alkyl)$_s$ aminoalkylamino; (alkyl)$_r$ aminocarbonyl-alkylamino; hydroxycarbonylalkylamino; alkylsulfonylamino; arylsulfonylamino; alkanoylaminoalkylamino; N-alkoxy-N-(alkyl)$_s$ amino; N-hydroxy-N-(alkyl)$_r$ amino; cyanoalkylamino; (alkenyl)$_r$ amino; alkoxyalkylamino; (alkynyl)$_r$ amino; alkenyloxy; alkynyloxy; or semicarbazido; or a group of formula

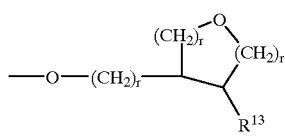

$R^{12}$ is hydrogen; alkyl; alkenyl; alkynyl, amino, formyl, alkylcarbonyl, alkoxycarbonyl or alkylsulfonyl;

$R^{13}$ is hydrogen; alkyl, alkoxy; alkenyloxy; alkynyloxy or alkanoyloxy;

M or Q is alkoxy; alkyl; (alkyl)$_r$ amino; hydroxy; hydrogen; alkenyloxy; (alkenyl)$_r$ amino; alkynyloxy; or (alkynyl)$_r$ amino;

W is oxygen, sulfur or N-alkoxy;

P is phosphorus;

| m | represents 1 or 2; |
|---|---|
| n | represents an integer from 1 to 4; |
| r | represents an integer from 0 to 2; |
| s | represents 0 or 1; |
| t | represents an integer from 0 to 6; and |
| z | represents 1 or 2. |

Particularly preferred compounds of formula I are those wherein $L^1$ and $L^2$ each independently represent hydrogen; halogen; nitro; amino; hydroxy; cyano; $C_{1-6}$-alkyl; $C_{1-6}$-alkoxyimino-$C_{1-6}$-alkyl; alkenyloxyimino-$C_{1-6}$-alkyl; $C_{2-8}$ alkenyloxyimino-$C_{1-6}$-alkoxycarbonyl-$C_{1-6}$-alkyl; $C_{1-6}$-alkoxycarbonyl-$C_{1-6}$-alkoxyimino-alkyl, hydroxy-$C_{1-6}$-alkyl; $C_{1-6}$-alkoxy-$C_{1-6}$-alkyl; di-($C_{1-6}$-alkoxy)-$C_{1-6}$-alkyl, di-(alkylthio)-alkyl, $C_{1-6}$-alkylsulfonylamino-$C_{1-6}$-alkyl; halo-$C_{1-6}$-alkylsulfonylamino-$C_{1-6}$-alkyl; ($C_{1-6}$-alkyl)n amino-$C_{1-6}$-alkyl; ($C_{1-6}$-alkylcarbonyloxy)$_z$-$C_{1-6}$-alkyl; halo-$C_{1-6}$-alkyl; cyano-$C_{1-6}$-alkyl, cyano-$C_{2-8}$-alkenyl formyl; $C_{1-6}$-alkylcarbonyl;

$ZR^8$ wherein Z is O, $NR^9$ or $S(O)_r$ or a single bond;

$R^8$ is $-(R^{10})_s-CWR^{11}$; $-(R^{10})_s-SO_2R^{11}$;

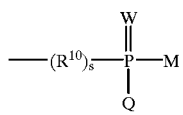

$C_{1-6}$-alkyl; halo-$C_{1-6}$-alkyl; hydroxy-$C_{1-6}$-alkyl; phenyl-$C_{1-6}$-alkyl; cyano-$C_{1-6}$-alkyl; $C_{1-6}$-alkanoyloxy-$C_{1-6}$-alkyl; $C_{1-6}$-alkoxy-$C_{1-6}$-alkyl; di-($C_{1-6}$-alkoxy)-$C_{1-6}$-alkyl $C_{3-8}$-cycolalkyl, $C_{2-8}$-alkenyl; or $C_{2-8}$-alkynyl;

$R^9$ is hydrogen; $C_{1-6}$-alkyl; $C_{2-8}$-alkenyl; $C_{2-8}$-alkynyl , formyl, amino or $C_{1-6}$-alkylcarbonyl;

$R^{10}$ is $NR^{12}$, $C_{1-4}$ alkylidene or $C_{2-4}$ alkenylidene;

$R^{11}$ is $C_{1-6}$-alkyl; halo-$C_{1-6}$-alkyl; halo-$C_{1-6}$-alkoxy, hydrogen; hydroxy; $C_{1-6}$-alkoxy; $C_{1-6}$-alkoxy-$C_{1-6}$-alkyl; $C_{1-6}$-alkoxy-$C_{1-6}$-alkoxy; $C_{1-6}$-alkoxy-$C_{1-6}$-alkylamino; di-$C_{1-6}$ alkoxy-$C_{1-6}$-alkylamino; phenyl, phenoxy; $C_{3-8}$-cycolalkyl, $C_{3-8}$-cycolalkoxy, phenyl-$C_{1-6}$-alkyl; $C_{1-6}$-alkoxycarbonyl; hydroxycarboxyl; $C_{1-6}$-alkoxycarbonyl-$C_{1-6}$-alkyl; $C_{1-6}$-alkoxycarbonyl-$C_{1-6}$-alkoxy, hydroxycarbonyl-$C_{1-6}$ alkyl; hydroxycarbonyl-$C_{1-6}$ alkoxy, ($C_{1-6}$-alkyl)$_r$ amino; ($C_{3-8}$-cycloalkyl)$_r$ amino; N-$C_{3-8}$-cycloalkyl-N-($C_{1-6}$-alkyl)$_s$ amino; ($C_{1-6}$-alkyl)$_r$ hydrazino; $C_{1-6}$-alkoxycarbonyl-$C_{1-6}$-alkylamino; hydroxy-$C_{1-6}$-alkylamino; ($C_{1-6}$-alkyl)$_r$ amino-$C_{1-6}$-alkylamino; ($C_{1-6}$-alkyl)$_r$ aminocarbonyl-$C_{1-6}$-alkylamino; hydroxycarbonyl-$C_{1-6}$-alkylamino; $C_{1-6}$-alkylsulfonylamino; phenylsulfonylamino; $C_{1-6}$-alkanoylamino-$C_{1-6}$-alkylamino; N-$C_{1-6}$-alkoxy-N-($C_{1-6}$-alkyl), amino; N-hydroxy-N-($C_{1-6}$-alkyl), amino; cyano-$C_{1-6}$-alkyl-amino; ($C_{2-8}$-alkenyl)$_r$ amino; $C_{1-6}$-alkoxy-$C_{1-6}$-alkylamino; ($C_{2-8}$-alkynyl)$_r$ amino; $C_{2-8}$-alkenyloxy; $C_{2-8}$-alkynyloxy; or semicarbazido;

$R^{12}$ is hydrogen; $C_{1-6}$-alkyl; $C_{2-8}$-alkenyl; $C_{2-8}$-alkynyl, formyl, $C_{1-6}$-alkylsulfonyl, $C_{1-6}$-alkylcarbonyloxy or $C_{1-6}$-alkylcarbonyl;

M or Q is $C_{1-6}$-alkoxy; $C_{1-6}$-alkyl; ($C_{1-6}$-alkyl)$_r$ amino; hydroxy; hydrogen; $C_{2-8}$-alkenyloxy; ($C_{2-8}$-alkenyl)$_r$ amino; $C_{2-8}$-alkynyloxy; or ($C_{2-8}$-alkynyl)$_r$ amino.

Especially preferred compounds of formula I include those wherein $NR^1R^2$ represents a substituted ind(az)ol-1-yl group of formula (2) having a substituent $L^2$ at the 4-position which is not hydrogen. These compounds have been found to be highly active against a broad range of grasses and broadleaf weeds, and to exhibit high selectivity in the crops soy beans and corn, i.e., these compounds produce desirably low phytotoxicity toward these crops while being very toxic to the weeds and grasses.

Other preferred embodiments of the present invention include:

(a) A compound of formula I, wherein $R^3$ represents an amino, a hydroxy or a methyl group, $R^4$ represents a halogen atom, or a cyano, a $C_{1-4}$ fluoroalkyl, a $C_{1-4}$ fluoroalkoxy or a $C_{1-4}$ fluoroalkylthio group, $R^5$ represents a hydrogen or halogen atom, or a methyl group.

(b) A compound of formulae IA or IB, (IA)

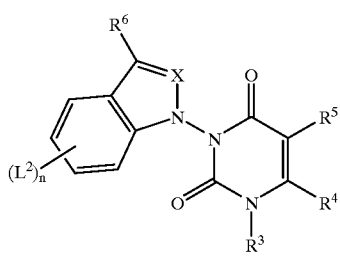

-continued (IB)

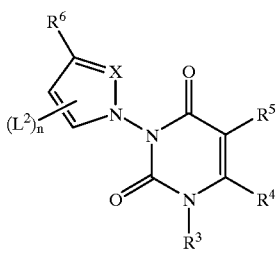

wherein $R^3$ through $R^6$, $L^2$, X and n are as described herein below and above, especially a heterocylcl-1yluracil of formula IA2.

(IA2)

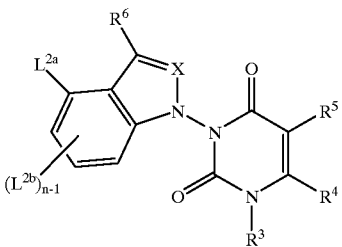

wherein $L^{2a}$ is not a hydrogen atom.

(c) A compound of formulae I, IA or IB, in which $R^4$ represents a trifluoromethyl group.

(d) A 3-heterocycl-1-yluracil compound selected from the group consisting of 1-15 methyl-3-(6-nitro-indol-1-yl)-6-trifluoromethyl-uracil, of 1-methyl-3-(5-nitro-indol-1-yl)-6-trifluoromethyl-uracil, 1-methyl-3-(6-methoxy-indol-1-yl)-6-trifluoromethyl-uracil, 1-methyl-3-(6-nitro-indazol-1-yl)-6-trifluoromethyl-uracil, 1-methyl-3-(5-nitro-indazol-1-yl)-6-trifluoromethyl-uracil, 1-methyl-3-(6-methoxy-indazol-1-yl)-6-trifluoromethyl-uracil, 1-methyl-3-(4-chloro-indol-1-yl)-6-trifluoromethyl-uracil and 1-methyl-3-(4-chloro-indazol-1-yl)-6-trifluoromethyl-uracil.

The compounds of this invention can be prepared according to known methods, particularly with the aid of the following methods:

Method (A): reacting an aminoalkenoate of the formula II, (II)

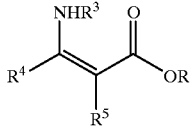

in which $R^3$ through $R^5$ have the meaning given, and R represents an alkyl, aryl or aralkyl group, with a heterocycl-1-ylcarbamate of formula III (III)

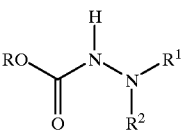

in which $R^1$ and $R^2$ have the meaning given, and R represents an alkyl, aryl or aralkyl group.

Method (B): reacting an oxazine of the formula IV, (IV)

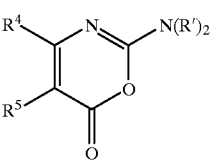

in which $R^4$ and $R^5$ have the meaning given, and R' represents a hydrogen atom or an alkyl, aryl or aralkyl group, with a heterocycl-1-ylamine of formula V (V)

$$\underset{H}{H}N-\underset{R^2}{N}-R^1$$

in which $R^1$ and $R^2$ have the meaning given, and
(b) optionally treating the resulting 3-heterocycl-1-yluracil of the formula (1C)

(1C)

$$\underset{R^2}{R^1}N-\underset{}{\overset{O}{\underset{\|}{C}}}\ldots$$

with an alkylating agent of formula VI $R^3$—LG  (VI)

in which $R^3$ has the meaning given, and
LG represents a suitable leaving group.

Those skilled in the art will readily understand and be able to select suitable leaving groups. These include but are not limited to, halogen, nitro, hydroxy, tosylate, mesylate, alkyl- or arylsulfonyl and alkyl- or arylsulfonyloxy groups.

In the event that $R^3$ represents an alkyl group, the compounds of formula I may be obtained by reaction of the compound of formula 1C, with an alkylating agent of formula VI, wherein $R^3$ represents an alkyl group such as alkylhalides, in particular alkylbromides or alkyliodides, or dialkylsulfates, in the presence of a base at a suitable temperature.

In the event that $R^3$ represents an amino group, the compounds of formula I may be obtained by reaction of the compound of formula 1C, with an nitrosylation agent followed by the reduction of the obtained N-nitrosamine or by reaction with 2,4-dinitrophenoxyamine in the presence of a base.

The nitrosylation reaction may be carried out in water, a dilute acid or an inert organic solvent at a suitable temperature.

The reaction with 2,4-dinitrophenoxyamine is as a rule carried out in an inert solvent.

The reactions mentioned hereinabove and herein below are conveniently carried out in an organic solvent. Generally, any inert organic solvent is suitable, preferably aliphatic, cycloaliphatic or aromatic hydrocarbons, which may be halogenated such as hexane, ligroine, petrol ethers, cyclohexane, benzene, toluene, xylene, di-, tri- or tetrachloromethane, ethylenechloride, trichloroethylene and chlorobenzene; ethers such as diethylether, methylethylether, methyl-tert-butylether, diisopropylether, dibutylether, tetrahydrofuran and dioxane; ketones such as acetone and butan-2-one; nitriles such as acetonitrile and propionitrile, carboxylic esters such as ethyl acetate and amyl acetate; carboxylic amides such as dimethylformamide, dimethylacetamide and N-methylpyrrolidone; sulfoxides such as dimethylsulfoxide; sulfone such as sulfolane.

Suitable bases are inorganic and organic bases such as potassium carbonate, sodium carbonate, potassium hydroxide, sodium hydroxide, sodium ethylate, sodium methylate, potassium tert-butylate, triethylamine, dimethylaminopyridine, pyridine, sodium hydride, sodium amide, butyllithium and lithium diisopropylamide.

The prepared compounds of formula I may be isolated and purified using conventional methods and techniques.

The starting compounds for the preparation of compounds of this invention are either known or can be prepared according to known methods.

The compounds of formula V may be obtained by a reacting a heterocyclic compound of formula VII

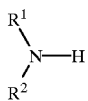

(VII)

wherein $R^1$ and $R^2$ have the meaning given with an amination agent such as O-mesitylsulfonyl-hydroxylamine or O-diphenylphosphinyl-hydroxylamine in the presence of a strong base and an inert solvent at a suitable temperature.

Suitable strong bases are inorganic and organic bases such as potassium tert-butylate, sodium hydride, hydride, sodium amide, potassium amide, methyllithium, butyllithium, lithium diisopropylamide and potassium hexamethyldisilazide.

The following acids are suitable for the preparation of the agronomically acceptable salts of the compounds of formula I: hydrohalides like hydrochloric or hydrobromic acid, phosphoric acid, nitric acid, sulfuric acid, mono- or bifunctional carboxylic acids and hydroxycarboxylic acids like acetic acid, maleic acid, succinic acid, fumaric acid, citric acid, salicylic acid, sorbic acid or lactic acid and sulfonic acids like p-toluenesulfonic acid or naphthalene-1,5-diyl-disulfonic acid. The agronomically acceptable salts of the compounds of formula I are prepared according to conventional salt formation procedures, for example by dilution of a compound of formula I in a suitable organic solvent, addition of an acid and isolation of the salt formed by, for example, filtration and optional purification by washing with an inert solvent.

The compounds of formula I have been found to have herbicidal activity. Accordingly, the invention further provides a herbicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into, e.g., emulsion or emulsifiable concentrates, solutions, oil in water emulsions, wettable powders, soluble powders, suspension concentrates, dusts, granules, water dispersible granules, aerosols, micro-capsules, gels and other formulation types by well-established procedures. These procedures may include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring and the type of composition may be chosen according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water, or mixtures thereof.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

Wettable powders of this invention suitably contain 5 to 90% w/w of active ingredient to solid inert carrier, 3 to 10% w/w of dispersing and wetting agents and, where necessary, 0 to 10% w/w of stabilizer(s) and/or other additives such as penetrants or stickers. Dusts may be formulated as a dust concentrate having a similar composition to that of a wettable powder but without a dispersant, and may be diluted in the field with further solid carrier to give a composition containing about 0.5 to 10% w/w of active ingredient. Water dispersible granules and granules suitably may be prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. Emulsifiable concentrates of this invention may contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are suitably milled so as to obtain a stable, non-sedimenting flowable product and contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystallization or as antifreeze agents.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| Active Ingredient | Compound of Example 4 | 30% (w/v) |
| Emulsifier(s) | e.g. Atlox ® 4856 B and Atlox ® 4857 B[1] | 5% (w/v) |
| Solvent | e.g. Shellsol ® A[2] | to 1000 ml |
| Suspension Concentrate (SC) | | |
| Active Ingredient | Compound of Example 4 | 50% (w/v) |
| Dispersing agent | e.g. Soprophor ® FL[3] | 3% (w/v) |

-continued

| | | |
|---|---|---|
| Antifoaming agent | e.g. Rhodorsil ® 422[3] | 0.2% (w/v) |
| Structure agent | e.g. Kelzan ® S[4] | 0.2% (w/v) |
| Antifreezing agent | e.g. Propylene glycol | 5% (w/v) |
| Biocidal agent | e.g. Proxel ®[5] | 0.1% (w/v) |
| Water | | to 1000 ml |

| Wettable Powder (WP) | | |
|---|---|---|
| Active Ingredient | Compound of Example 4 | 60% (w/w) |
| Wetting agent | e.g. Atlox ® 4995[1] | 2% (w/w) |
| Dispersing agent | e.g. Witcosperse ® D-60[6] | 3% (w/w) |
| Carrier/Filler | e.g. Kaolin | 35% (w/w) |
| Water Dispersible Granules | | |
| Active Ingredient | Compound of Example 4 | 50% (w/w) |
| Dispersing/Binding agent | e.g. Witcosperse ® D-450[6] | 8% (w/w) |
| Wetting agent | e.g. Morwet ® EFW[6] | 2% (w/w) |
| Antifoaming agent | e.g. Rhodorsil ® EP 6703[3] | 1% (w/w) |
| Disintegrant | e.g. Agrimer ® ATF[7] | 2% (w/w) |
| Carrier/Filler | e.g. Kaolin | 35% (w/w) |

[1]Product commercially available from ICI Surfactants
[2]Product commercially available from Deutsche Shell AG
[3]Product commercially available from Rhône-Poulenc
[4]Product commercially available from Kelco Co.
[5]Product commercially available from Zeneca
[6]Product commercially available from Witco
[7]Product commercially available from International Speciality Products The compositions of this invention can also comprise other compounds having biological activity, e.g. compounds having similar or complementary pesticidal activity or compounds having plant growth regulating, fungicidal or insecticidal activity. These mixtures of pesticides can have a broader spectrum of activity than the compound of formula I alone. Furthermore, the other pesticide can have a synergistic effect on the pesticidal activity of the compound of formula I.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used: ametrydione, metabenzthiazuron, metamitron, metribuzin, 2,4-D, 2,4-DB, 2,4-DP, alachlor, alloxydim, asulam, atrazin, bensulfuron, bentazon, bifenox, bromoxynil, butachlor, chloridazon, chlorimuron, chlorpropham, chlorsulfuron, chlortoluron, cinmethylin, clopyralid, cyanazin, cycloate, cycloxydim, dichlobenil, diclofop, eptame, ethiozin, fenoxaprop, fluazifop, fluometuron, fluridone, fluroxypyr, fomesafen, glyphosate, haloxyfop, hexazinone, imazamethabenz, imazapyr, imazaquin, imazethapyr, ioxynil, isoproturon, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofopethyl, sethoxydim, simetryne, terbutryne, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, thiameturon, thifensulfuron, triasulfuron, oxasulfuron, azimsulfuron, tribenuron, esprocarb, prosulfocarb, terbutylazin, benfuresate, clomazone, di-methazone, dithiopyr, isoxaben, quinchlorac, qinmerac, sulfosate, cyclosulfamuron, imazamox, imazamethapyr, flamprop-M-methyl, flamprop- M-isopropyl, picolinafen, thiafluamide, isoxaflutole, flurtamone, daimuron, bromobutide, methyidimron, dimethenamid, sulcotrione, sulfentrazone, oxadiargyl, acifluorfen, cafenstrole, carfentrazone, diuron, glufosinate.

Mixtures with other active ingredients like fungicides, insecticides, acaricides, and nematicides are possible.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the invention.

EXAMPLE 1

6-Methoxy-1-(3-methyl-4-trifluoromethylpyrimidin-2,6-dion-1-yl)-indole

1A N-Amino-6-methoxyindole

A mixture of 0.735 g 6-methoxyindole and 5 ml tetrahydrofuran (THF) is added to a suspension of 0.44 g of 60% sodium hydride in 10 ml THF at 0° C. After 15 minutes a mixture 1.07 g O-mesitylsulfonyl-hydroxylamine and 15 ml THF is added. Stirring at 0° C. is continued for 1.5 hours. The mixture is poured into ice cold water, extracted with ethyl acetate, and purified by flash chromatography.

Yield: 0.2 g 1B 6-Methoxy-1-(4-trifluoromethylpyrimidin-2,6-dion-1-yl)-indole

A mixture of 0.2 g 1A, 0.268 g 2-dimethylamino-4-trifluoromethyl-1,3-oxazin-6-one (obtained according to M.-A. Decock-Plancquaert et al., Bull. Soc. Chim. Belg. 101 (4) 313–321 (1992)) and 10 ml acetic acid is refluxed for 4 hours. The mixture is poured into water, extracted and chromatographed to yield 0.23 g of 1B as an oil.

1C 6-Methoxy-1-(3-methyl-4-trifluoromethylpyrimidin-2,6-dion-1-yl)-indole

A mixture of 0.2 g 1B, 0.25 g potassium carbonate and 15 ml acetonitrile is treated with 0.2 g methyl iodide at room temperature. After stirring over night the mixture is poured into water, acidified with aqueous hydrochloric acid and extracted with ethyl acetate.

Yield: 0.18 g with m.p.60–63° C.

EXAMPLE 2

6-Methoxy-1-(3-amino4-trifluoromethylpyrimidin-2,6-dion-1-yl)-indole

A mixture of 1.45 g 1B and 5 ml tetrahydrofuran (THF) is added to a suspension of 0.44 g of 60% sodium hydride in 10 ml THF at 0° C. After 15 minutes a mixture 1.07 g O-mesitylsufonyl-hydroxylamine and 15 ml THF is added. Stirring at 0° C. is continued for 1.5 hours. The mixture is poured into ice cold water, extracted with ethyl acetate, and purified by flash chromatography.

EXAMPLE 3

6-Amino-1-(3-methyl-4-trifluoromethylpyrimidin-2,6-dion-1-yl)-indole

6-Nitro-1-(3-methyl-4-trifluoromethylpyrimidin-2,6-dion-1-yl)-indole (3.5 g, obtained analogously to Example 1C) is dissolved in a mixture of ethyl acetate (100 mL) and ethanol (50 mL), Pd/C (10%wt) catalyst is added. A hydrogen pressure of 60 psi is applied and the hydrogenation is performed at room temperature. After removal of the hydrogenation catalyst by filtration and removal of the solvent by evaporation the amine was obtained after flash chromatography: 1.8 g, m.p. 181–184 1° C.

This compound can be modified according to standard procedures as for example by acylation or sulfonylation of the amino group.

EXAMPLES 4–110

The compounds listed in TABLE 1 can be prepared by methods analogeous to those described in examples 1, 2 or 3 and according to the methods described in the foregoing description.

TABLE 1

Compounds of formula IA1

(IA1)

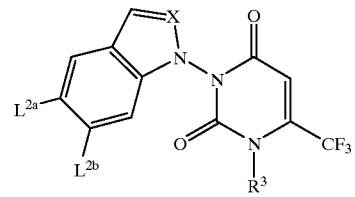

| Example | $L^{2a}$ | $L^{2b}$ | $R^3$ | X | m.p.(° C.) |
|---|---|---|---|---|---|
| 4 | $NO_2$ | H | $CH_3$ | CH | 110–113 |
| 5 | H | $NO_2$ | $CH_3$ | CH | 185–190 |
| 6 | H | Br | $CH_3$ | CH | 157–160 |
| 7 | $NO_2$ | H | $CH_3$ | N | 193–196 |
| 8 | H | $EtO_2CCH(CH_3)O$ | $CH_3$ | N | |
| 9 | H | $HC\equiv CCH(CH_3 3)O$ | $CH_3$ | N | |
| 10 | $NO_2$ | Cl | $CH_3$ | CH | |
| 11 | $NO_2$ | $CH_3O$ | $CH_3$ | CH | |
| 12 | $NO_2$ | $NO_2$ | $CH_3$ | CH | |
| 13 | H | $NHCOCH_3$ | $CH_3$ | CH | |
| 14 | H | $NHSO_2CH_3$ | $CH_3$ | CH | |
| 15 | H | $NHCOCF_3$ | $CH_3$ | CH | 292–295 |

TABLE 1-continued

Compounds of formula IA1

(IA1)

[Structure of formula IA1]

| Example | L$^{2a}$ | L$^{2b}$ | R$^3$ | X | m.p.(° C.) |
|---|---|---|---|---|---|
| 16 | H | NHSO$_2$CH$_2$Cl | CH$_3$ | CH | 110–113 |
| 17 | NO$_2$ | Cl | CH$_3$ | N | 251–253 |
| 18 | NO$_2$ | CH$_3$O | CH$_3$ | N | |
| 19 | NO$_2$ | NO$_2$ | CH$_3$ | N | |
| 20 | H | NHCOCH$_3$ | CH$_3$ | N | |
| 21 | H | NH | CH$_3$ | N | |
| 22 | H | NHSO$_2$CH$_3$ | CH$_3$ | N | |
| 23 | H | NHCOCF$_3$ | CH$_3$ | N | |
| 24 | H | NHSO$_2$CF$_3$ | CH$_3$ | N | |
| 25 | CH$_3$O | H | NH$_2$ | CH | |
| 26 | NO$_2$ | H | NH$_2$ | CH | |
| 27 | H | NO$_2$ | NH$_2$ | CH | |
| 28 | H | Br | NH$_2$ | CH | |
| 29 | NO$_2$ | H | NH$_2$ | N | |
| 30 | H | EtO$_2$CCH(CH$_3$)O | NH$_2$ | N | |
| 31 | H | HC≡CCH(CH$_3$)O | NH$_2$ | N | |
| 32 | NO$_2$ | Cl | NH$_2$ | CH | |
| 33 | NO$_2$ | CH$_3$O | NH$_2$ | CH | |
| 34 | CH$_3$O | H | C$_2$H$_5$ | CH | |
| 35 | NO$_2$ | H | C$_2$H$_5$ | CH | |
| 36 | H | CH$_3$O | C$_2$H$_5$ | CH | |
| 37 | H | NO$_2$ | C$_2$H$_5$ | CH | |
| 38 | H | Br | C$_2$H$_5$ | CH | |
| 39 | NO$_2$ | H | C$_2$H$_5$ | N | |
| 40 | H | EtO$_2$CCH(CH$_3$)O | C$_2$H$_5$ | N | |
| 41 | H | HC≡CCH(CH$_3$)O | C$_2$H$_5$ | N | |
| 42 | NO$_2$ | Cl | C$_2$H$_5$ | CH | |
| 43 | NO$_2$ | CH$_2$O | C$_2$H$_5$ | CH | |
| 44 | NO$_2$ | Cl | C$_3$H$_7$ | CH | |
| 45 | NO$_2$ | CH$_3$O | C$_3$H$_7$ | CH | |
| 46 | CH$_3$O | H | C$_2$H$_5$ | CH | |
| 47 | NO$_2$ | H | C$_3$H$_7$ | CH | |
| 48 | H | CH$_3$O | C$_3$H$_7$ | CH | |
| 49 | NO$_2$ | H | C$_4$H$_9$ | CH | |
| 50 | NO$_2$ | H | H | CH | 225 (dec) |
| 51 | H | NO$_2$ | H | CH | >200 (dec) |
| 52 | H | Br | H | CH | 205 (dec) |
| 53 | NO$_2$ | H | H | N | 290–295 |
| 54 | H | EtO$_2$CCH(CH$_3$)O | H | N | |
| 55 | H | HC≡CCH(CH$_3$)O | H | N | |
| 56 | NO$_2$ | Cl | H | CH | |
| 57 | NO$_2$ | CH$_3$O | H | CH | |
| 58 | NO$_2$ | NO$_2$ | H | CH | |
| 59 | H | NHCOCH$_3$ | H | CH | |
| 60 | H | NH$_2$ | H | CH | |
| 61 | H | NHSO$_2$CH$_3$ | H | CH | |
| 62 | NO$_2$ | Cl | H | N | |
| 63 | NO$_2$ | CH$_3$O | H | N | |
| 64 | NO$_2$ | NO$_2$ | H | N | |
| 65 | H | NHCOCH$_3$ | H | N | |
| 66 | H | NH$_2$ | H | N | |
| 67 | H | NHSO$_2$CH$_3$ | H | N | |
| 68 | H | NHCOCF$_3$ | H | N | |
| 69 | H | CHCOCF$_3$ | H | CH | |
| 70 | H | NHSO$_2$CF$_3$ | H | N | |
| 71 | H | O-cyclopentyl | H | N | |
| 72 | H | NH—CH(CH3)—C≡CH | H | N | |
| 73 | H | —CO$_2$—C(CH$_3$)$_2$—CO$_2$CH$_3$ | H | N | |
| 74 | H | —CO$_2$—C(CH$_3$)$_2$—CONCH$_2$CH=CH$_2$ | H | N | |
| 75 | H | NH—CO—CH$_2$—O—COCH$_3$ | H | N | |
| 76 | H | O-cyclopentyl | H | CH | |
| 77 | H | NH—CH(CH3)—C≡CH | H | CH | |
| 78 | H | —CO$_2$—C(CH$_3$)$_2$—CO$_2$CH$_3$ | H | CH | |
| 79 | H | —CO$_2$—C(CH$_3$)$_2$—CONCH$_2$CH=CH$_2$ | H | CH | |

TABLE 1-continued

Compounds of formula IA1

(IA1)

| Example | L$^{2a}$ | L$^{2b}$ | R$^3$ | X | m.p.(° C.) |
|---|---|---|---|---|---|
| 80 | H | NH—CO—CH$_2$—O—COCH$_3$ | H | CH | |
| 81 | Cl | H | CH$_3$ | CH | |
| 82 | Cl | CH$_3$O | CH$_3$ | CH | |
| 83 | Cl | NO$_2$ | CH$_3$ | CH | |
| 84 | Cl | Br | CH$_3$ | CH | |
| 85 | Cl | H | CH$_3$ | N | |
| 86 | Cl | EtO$_2$CCH(CH$_3$)O | CH$_3$ | N | |
| 87 | Cl | HC≡CCH(CH$_3$)O | CH$_3$ | N | |
| 88 | Cl | CH$_3$O | CH$_3$ | N | |
| 89 | Cl | Cl | CH$_3$ | CH | |
| 90 | Cl | NHCOCH$_3$ | CH$_3$ | CH | |
| 91 | CN | H | CH$_3$ | N | 198–202 |
| 92 | CN | CH$_3$O | CH$_3$ | CH | |
| 93 | CN | NO$_2$ | CH$_3$ | CH | |
| 94 | CN | Br | CH$_3$ | CH | |
| 95 | CN | H | CH$_3$ | N | |
| 96 | CN | EtO$_2$CCH(CH$_3$)O | CH$_3$ | N | |
| 97 | CN | HC≡CCH(CH$_3$)O | CH$_3$ | N | |
| 98 | CN | CH$_3$O | CH$_3$ | N | |
| 99 | CN | Cl | CH$_3$ | CH | |
| 100 | CN | NHCOCH$_3$ | CH$_3$ | CH | |
| 101 | Br | NHCOCH$_3$ | CH$_3$ | CH | |
| 102 | H | NHCOCH$_2$—O—CO—CH$_3$ | CH$_3$ | CH | 190–193 |
| 103 | H | NHSO$_2$—CH(CH$_3$)$_2$ | CH$_3$ | CH | 130–135 |
| 104 | Cl | Cl | CH$_3$ | N | 190–195 |
| 105 | H | OCH$_2$—(4F)—C$_6$H$_4$ | CH$_3$ | N | 208–210 |
| 106 | H | OCH$_2$CH=CH$_2$ | CH$_3$ | N | 212–214 |
| 107 | Br | H | CH$_3$ | N | 153–156 |
| 108 | H | OCH$_2$CH=CH$_2$ | CH$_3$ | N | 215–218 |
| 109 | H | OCH$_2$CH=CCl$_2$ | CH$_3$ | N | 141–144 |
| 110 | H | Cl | CH$_3$ | CH | Oil |

EXAMPLES 111–167

The compounds listed in TABLE 2 can be prepared by methods anologous to those described in examples 1, 2 or 3 and according to the methods described in the foregoing description.

TABLE 2

Compounds of formula IB1

(IB1)

| Example | L$^{2a}$ | L$^{2b}$ | R$^3$ | X | m.p. (° C.) |
|---|---|---|---|---|---|
| 111 | NO$_2$ | NH$_2$ | CH$_3$ | CH | |
| 112 | NO$_2$ | NH—CH(CH$_3$)—C≡CH | CH$_3$ | CH | |
| 113 | NO$_2$ | NHCOCH$_3$ | CH$_3$ | CH | |
| 114 | NO$_2$ | NHSO$_2$CH$_3$ | CH$_3$ | CH | |
| 115 | NO$_2$ | NHCOCF$_3$ | CH$_3$ | CH | |
| 116 | NO$_2$ | NHCOCH$_2$Cl | CH$_3$ | CH | |
| 117 | NO$_2$ | NHCH$_2$CH=CH$_2$ | CH$_3$ | CH | |
| 118 | NO$_2$ | H | CH$_3$ | N | 128 |
| 119 | NO$_2$ | NH$_2$ | CH$_3$ | N | |
| 120 | NO$_2$ | NH—CH(CH$_3$)—C≡CH | CH$_3$ | N | |
| 121 | NO$_2$ | NHCOCH$_3$ | CH$_3$ | N | |
| 122 | NO$_2$ | NHSO$_2$CH$_3$ | CH$_3$ | N | |
| 123 | NO$_2$ | NHCOCF$_3$ | CH$_3$ | N | |
| 124 | NO$_2$ | NHCOCH$_2$Cl | CH$_3$ | N | |
| 125 | NO$_2$ | NHCH$_2$CH=CH$_2$ | CH$_3$ | N | |

TABLE 2-continued

Compounds of formula IB1

(IB1)

| Example | L$^{2a}$ | L$^{2b}$ | R$^3$ | X | m.p. (° C.) |
|---|---|---|---|---|---|
| 126 | CN | NH$_2$ | CH$_3$ | CH | |
| 127 | CN | NH—CH(CH$_3$)—C≡CH | CH$_3$ | CH | |
| 128 | CN | NHCOCH$_3$ | CH$_3$ | CH | |
| 129 | CN | NHSO$_2$CH$_3$ | CH$_3$ | CH | |
| 130 | CN | NHCOCF$_3$ | CH$_3$ | CH | |
| 131 | CN | NHCOCH$_2$Cl | CH$_3$ | CH | |
| 132 | CN | NHCH$_2$CH=CH$_2$ | CH$_3$ | CH | |
| 133 | CN | NH$_2$ | CH$_3$ | N | >200 |
| 134 | CN | NH—CH(CH$_3$)—C≡CH | CH$_3$ | N | |
| 135 | CN | NHCOCH$_3$ | CH$_3$ | N | |
| 136 | CN | NHSO$_2$CH$_3$ | CH$_3$ | N | |
| 137 | CN | NHCOCF$_3$ | CH$_3$ | N | |
| 138 | CN | NHCOCH$_2$Cl | CH$_3$ | N | |
| 139 | CN | NHCH$_2$CH=CH$_2$ | CH$_3$ | N | |
| 140 | NO$_2$ | NH$_2$ | NH$_2$ | CH | |
| 141 | NO$_2$ | NH—CH(CH$_3$)—C≡CH | NH$_2$ | CH | |
| 142 | NO$_2$ | NHCOCH$_3$ | NH$_2$ | CH | |
| 143 | NO$_2$ | NHSO$_2$CH$_3$ | NH$_2$ | CH | |
| 144 | NO$_2$ | NHCOCF$_3$ | NH$_2$ | CH | |
| 145 | NO$_2$ | NHCOCH$_2$Cl | NH$_2$ | CH | |
| 146 | NO$_2$ | NHCH$_2$CH=CH$_2$ | NH$_2$ | CH | |
| 147 | NO$_2$ | NH$_2$ | NH$_2$ | N | |
| 148 | NO$_2$ | NH—CH(CH$_3$)—C≡CH | NH$_2$ | N | |
| 149 | NO$_2$ | NHCOCH$_3$ | NH$_2$ | N | |
| 150 | NO$_2$ | NHSO$_2$CH$_3$ | NH$_2$ | N | |
| 151 | NO$_2$ | NHCOCF$_3$ | NH$_2$ | N | |
| 152 | NO$_2$ | NHCOCH$_2$Cl | NH$_2$ | N | |
| 153 | NO$_2$ | NHCH$_2$CH=CH$_2$ | NH$_2$ | N | |
| 154 | CN | NH$_2$ | NH$_2$ | CH | |
| 155 | CN | NH—CH(CH$_3$)—C≡CH | NH$_2$ | CH | |
| 156 | CN | NHCOCH$_3$ | NH$_2$ | CH | |
| 157 | CN | NHSO$_2$CH$_3$ | NH$_2$ | CH | |
| 158 | CN | NHCOCF$_3$ | NH$_2$ | CH | |
| 159 | CN | NHCOCH$_2$Cl | NH$_2$ | CH | |
| 160 | CN | NHCH$_2$CH=CH$_2$ | NH$_2$ | CH | |
| 161 | CN | NH$_2$ | NH$_2$ | N | |
| 162 | CN | NH—CH(CH$_3$)—C≡CH | NH$_2$ | N | |
| 163 | CN | NHCOCH$_3$ | NH$_2$ | N | |
| 164 | CN | NHSO$_2$CH$_3$ | NH$_2$ | N | |
| 165 | CN | NHCOCF$_3$ | NH$_2$ | N | |
| 166 | CN | NHCOCH$_2$Cl | NH$_2$ | N | |
| 167 | CN | NHCH$_2$CH=CH$_2$ | NH$_2$ | N | |

EXAMPLE 168

3-(4-Chloro-1-indazol-1-yl)-1-methyl-6trifluoromethylpyrimidine-2,4-dione

168A Preparation of 4-Chloro-indazol-1-ylamine

Sodium hydride (60 % wt suspension in mineral oil; 0.33 g, 8.3 mmol) is suspended in dry tetrahydrofuran (THF, 10 mL) and is cooled to 0° C. A mixture of 4-chloroindazole (1.05 g, 6.9 mmol) and THF (10 mL) is added to the slurry at 4° C. After the addition is completed, the mixture is stirred for 30 min. Then a mixture of O-mesitylenesulfonylhydroxylamine (1.25 g, 7 mmol) and THF (10 mL) is added slowly, at a temperature below 5° C. After the addition is completed, the reaction mixture is allowed to reach room temperature and is subsequently stirred for 3 h. Then the mixture is cooled again to 0° C., and a second aliquot of O-mesitylenesulfonylhydroxylamine (1.25 g, 7 mmol) in THF (10 mL) is added slowly. The mixture is allowed to reach ambient temperature and is subsequently stirred overnight. The reaction mixture is worked up by adding it to water, extracting into ethyl acetate, and drying over sodium sulfate. The crude product (1.2 g) is obtained after filtration of the drying agent and evaporation of the solvent. This material is used for the next reaction step without purification.

168B Preparation of 3-(4-chloro-indazol-1-yl)-6-trifluoromethyl-1H-pyrimidine-2,4-dione The crude 168A (1.15 g, 6.88 mmol assumed) is dissolved in glacial acetic acid (15 mL) and 2-dimethylamino4-trifluoromethyl-[1,3]oxazin-6-one (1.43 g, 6.88 mmol) is added. The mixture was stirred for 4 h under reflux, after which the acetic acid iss removed in vacuo. The residue is dissolved in ethyl acetate, washed with saturated sodium carbonate solution and water, and is subsequently dried over sodium sulfate. The crude product (1.9 g) is obtained after removal of the drying agent by filtration and evaporation of the solvent. The product (100 mg) is purified by flash chromatography (ethyl acetate/petrol ether 3/7).

168C Preparation of 3-(4-Chloro-indazol-1-yl)-1-methyl-6-trifluoromethylpyrimidine-2,4-dione A mixture of 168B (100 mg, 0.3 mmol), dry acetonitril (3 mL), potassium carbonate (0.05 g, 0.33 mmol) and methyl iodide (0.1 g, 0.7 mmol) is stirred overnight at room temperature. The solids are removed by filtration. The motherliquor is concentrated under reduced pressure. The residue obtained is purified by flash chromatography (ethyl acetate/petrol ether 3/7) which yields the product as an orange semi-solid (41 mg).

EXAMPLE 169

3-(4-Chloro-indol-1-yl)-1-methyl-6-trifluoromethylpyrimidine-2,4-dione

169A Preparation of 4-Chloro-indol-1-ylamine

Sodium hydride (60 %wt suspension in mineral oil; 0.86 g, 21.5 mmol) is suspended in dry tetrahydrofuran (THF, 20 mL) and is cooled to 0° C. A mixture of 4-chloroindole (2.5 g, 16.5 mmol) and THF (10 mL) is added to the slurry at 4° C. After the addition is completed, the mixture is stirred for 30 min. Then a mixture of O-mesitylenesulfonylhydroxylamine (3.02 g, 14 mmol) and THF (25 mL) is added slowly at a temperature below 5° C. After the addition is completed, the reaction mixture is allowed to reach room temperature and is subsequently stirred for 3 h. Then the mixture is cooled again to 0° C., and a second aliquot of O-mesitylenesulfonylhydroxylamine (3.02 g, 14 mmol) in THF (25 mL) is added slowly. The mixture is allowed to reach ambient temperature and was subsequently stirred overnight. The reaction mixture is worked up by adding it to water, extracting into ethyl acetate, and drying over sodium sulfate. The crude product (4 g) is obtained after filtration of the drying agent and evaporation of the solvent. The aminated indole (2,2 g) is obtained as a black oil (mixture of starting material and product) after flash chromatography, using toluene as eluent.

169B Preparation of 3-(4-chloro-indol-1-yl)-6-trifluoromethyl-1H-pyrimidine-2,4-dione A mixture of 169A, glacial acetic acid (30 mL) and 2-dimethylamino-4-trifluoromethyl-[1,3]oxazin-6-one (2.76 g, 13.3 mmol) is stirred for 4.5 h under reflux, whereupon the acetic acid was removed in vacuo. The residue is diluted with ethyl acetate, washed with water and subsequently dried over sodium sulfate. The crude product (3 g) is obtained after removal of the drying agent by filtration and evaporation of the solvent. The product (0.88 g) is obtained as a brown oil after flash chromatography (ethyl acetate/petrol ether 2/8).

169C Preparation of 3-(4-chloro-indol-1-yl)-1-methyl-6-trifluoromethylpyrimidine-2,4-dione A mixture of 169B (0.88 g, 2.7 mmol), dry acetonitril (10 mL), potassium carbonate (0.41 g, 2.9 mmol) and methyl iodide (0.88 g, 6.2 mmol) is stirred overnight at room temperature. The solids are removed by filtration. The motherliquor is concentrated under reduced pressure. The residue obtained is purified by flash chromatography (ethyl acetate/petrol ether 2/8) to yield the product as a brown oil (0.23 g).

EXAMPLES 170–209

The compounds listed in TABLE 3 can be prepared by methods analogous to those described in examples 168 and 169 and according to the methods described in the foregoing description.

TABLE 3

Compounds of formula IA2a

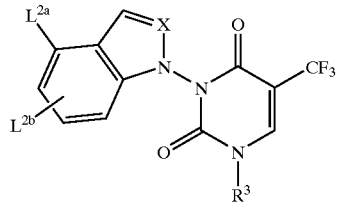

(IA2a)

| Example | L2a | L2b | R3 | X | m.p. (° C.) |
|---|---|---|---|---|---|
| 170 | Cl | 5-NH2 | CH3 | CH | |
| 171 | Cl | 5-NH—CH(CH3)—C≡CH | CH3 | CH | |
| 172 | Cl | 5-NHCOCH3 | CH3 | CH | |
| 173 | Cl | 5-NHSO2CH3 | CH3 | CH | |
| 174 | Cl | 5-NHCOCF3 | CH3 | CH | |
| 175 | Cl | 5-NHCOCH2Cl | CH3 | CH | |
| 176 | Cl | 5-NHCH2CH=CH2 | CH3 | CH | |
| 177 | Cl | 5-Cl | CH3 | CH | |
| 178 | Cl | 5-CH3 | CH3 | CH | |
| 179 | Cl | 5-OCH3 | CH3 | CH | |
| 180 | Cl | 5-Cl | NH2 | CH | |
| 181 | Cl | 5-OCF3 | CH3 | CH | |
| 182 | Cl | 5-OCH(CH3)2 | CH3 | CH | |
| 183 | Cl | H | NH2 | CH | |
| 184 | F | H | CH3 | CH | |
| 185 | Br | H | CH3 | CH | |
| 186 | CH3 | H | CH3 | CH | |
| 187 | OCH3 | H | CH3 | CH | |
| 188 | NO2 | H | CH3 | CH | |
| 189 | CN | H | CH3 | CH | |
| 190 | Cl | 5-NH2 | CH3 | N | |
| 191 | Cl | 5-NH—CH(CH3)—C≡CH | CH3 | N | |
| 192 | Cl | 5-NHCOCH3 | CH3 | N | |
| 193 | Cl | 5-NHSO2CH3 | CH3 | N | |
| 194 | Cl | 5-NHCOCF3 | CH3 | N | |
| 195 | Cl | 5-NHCOCH2Cl | CH3 | N | |
| 196 | Cl | 5-NHCH2CH=CH2 | CH3 | N | |
| 197 | Cl | 5-Cl | CH3 | N | |
| 198 | Cl | 5-CH3 | CH3 | N | |
| 199 | Cl | 5-OCH3 | CH3 | N | |
| 200 | Cl | 5-Cl | NH2 | N | |
| 201 | Cl | 5-OCF3 | CH3 | N | |
| 202 | Cl | 5-OCH(CH3)2 | CH3 | N | |
| 203 | Cl | H | NH2 | N | |
| 204 | F | H | CH3 | N | |
| 205 | Br | H | CH3 | N | |
| 206 | CH3 | H | CH3 | N | |
| 207 | OCH3 | H | CH3 | N | |
| 208 | NO2 | H | CH3 | N | |

TABLE 3-continued

Compounds of formula IA2a

| Example | L2a | L2b | R3 | X | m.p. (° C.) |
|---|---|---|---|---|---|
| 209 | CN | H | CH3 | N | |

Herbicidal Activity

To evaluate their herbicidal activity, compounds according to the invention are tested using a representative range of plants:

| Crops | |
|---|---|
| TRZAW | Triticum aestivum |
| HORVW | Hordeum vulgare |
| ZEAMX | Zea mays |
| GLXMA | Glycine max |
| Weed | |
| ALOMY | Alopecurus myosuroides |
| IPOHE | Ipomoea hederacea |
| GALAP | Galium aparine |
| ABUTH | Abutilon theophrasti |
| STEME | Stellaria media |
| MATIN | Matricaria inodora |
| ECHCG | Echinochloa crus-galli |
| SETVI | Setaria viridis |

The pre-emergence tests involve spraying a liquid formulation of the compound onto the soil in which the seeds of the plant species mentioned above has recently been sown.

The soil used in the tests is a prepared horticultural loam. The formulations used in the tests are prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels corresponding to 1000 g and 250 g/ha of active material per hectare in a volume equivalent to 900 litres per hectare. In these tests untreated sown soil are used as controls.

The post-emergence herbicidal activity of the compounds of the present invention is demonstrated by the following test, wherein monocotyledonous and dicotyledonous plants are treated with formulations prepared from solutions of the test compounds in acetone containing 0.4 % by weight of an alkylphenol/ethylene oxide condensate available under the trade mark TRITON X-155. These acetone solutions are diluted with water and the resulting formulations applied at dosage levels equivalent to about 1000, 800, 400, 250 or 100 g/ha per hectare of test compound per pot. After spraying, the plants are placed on greenhouse benches and are cared for in the usual manner, commensurate with conventional greenhouse practices.

The herbicidal effects of the test compounds are assessed visually twenty-one days after spraying the foliage and the soil and are recorded on a 0–9 scale. A rating 0 indicates growth as untreated control, a rating 9 indicates death. An increase of 1 unit on the linear scale approximates to a 10% increase in the level of effect.

The results of the first assessment are set out in TABLES 4 through 6.

TABLE 4

Pre- and post-emergence activity

| Example | Rate G/ha | Timing | T R Z A W | H O R V W | Z E A M X | G L X M A | S E T V I | E C H C G | A L O M Y | I P O H E | G A L A P | A B U T H | S T E M E | M A T I N |
|---|---|---|---|---|---|---|---|---|---|---|---|---|---|---|
| 1 | 1000 | PRE | 9 | 9 | 9 | 6 | 9 | 9 | 9 | 9 | 9 | 9 | 9 | 9 |
|   | 250  | PRE | 8 | 7 | 8 | 6 | 9 | 9 | 9 | 8 | 9 | 9 | 9 | 9 |
| 4 | 800  | PRE | 6 | 7 | 8 | 3 | 9 | 8 | — | 8 | 9 | 9 | 9 | 9 |
|   | 400  | PRE | 3 | 5 | 6 | 3 | 9 | 8 | — | 7 | 9 | 9 | 9 | 9 |
| 5 | 1000 | PRE | 5 | 6 | 5 | 0 | 8 | 8 | 6 | 5 | 8 | 9 | 2 | 8 |
|   | 250  | PRE | 2 | 4 | 4 | 0 | 8 | 7 | 3 | 5 | 5 | 5 | 0 | 7 |
| 6 | 400  | PRE | 0 | 1 | 4 | 0 | 8 | 5 | 3 | 2 | 9 | 8 | 4 | 5 |
|   | 100  | PRE | 0 | 0 | 2 | 0 | 5 | 1 | 1 | 1 | 2 | 6 | 1 | 1 |
| 1 | 1000 | POST | 8 | 8 | 9 | 9 | 9 | 9 | 9 | 9 | 9 | 9 | 9 | 9 |
|   | 250  | POST | 6 | 8 | 9 | 9 | 9 | 9 | 9 | 9 | 9 | 9 | 9 | 8 |
| 4 | 800  | POST | 4 | 6 | 8 | 8 | 9 | 9 | 9 | 9 | 9 | 9 | 9 | 9 |
|   | 400  | POST | 4 | 5 | 6 | 8 | 9 | 8 | 8 | 9 | 8 | 9 | 9 | 9 |
| 5 | 1000 | POST | 2 | 4 | 5 | 8 | 8 | 8 | 4 | 9 | 6 | 9 | 5 | 7 |
|   | 250  | POST | 0 | 2 | 2 | 6 | 7 | 5 | 1 | 6 | 4 | 8 | 0 | 4 |
| 6 | 400  | POST | 3 | 3 | 3 | 8 | 9 | 8 | 4 | 9 | 8 | 9 | 8 | 5 |
|   | 100  | POST | 2 | 3 | 2 | 4 | 7 | 4 | 2 | 8 | 5 | 9 | 5 | 3 |

PRE: pre-emergence application
POST: post-emergence application

TABLE 5

Pre- and post-emergence activity

| Example | Rate g/ha | Timing | T R Z A W | Z E A M X | S E T V I | E C H C G | A M B E Y | I P O H E | G A L A P | A B U T H | S T E M E | M A T I N |
|---|---|---|---|---|---|---|---|---|---|---|---|---|
| 7 | 400 | PRE  | 4 | 4 | 9 | 8 | 6 | 9 | 8 | 9 | 9 | 9 |
|   | 100 | PRE  | 1 | 0 | 8 | 7 | 3 | 7 | 4 | 9 | 5 | 9 |
| 7 | 400 | POST | 3 | 5 | 9 | 8 | 6 | 9 | 9 | 9 | 9 | 9 |
|   | 100 | POST | 1 | 3 | 9 | 7 | 4 | 9 | 8 | 9 | 8 | 8 |
|   | 25  | POST | 0 | 2 | 8 | 2 | 2 | 9 | 6 | 8 | 4 | 7 |

The indazole uracil of Example 7, showed good performance both in pre- and post-emergence. In pre-emergence all of the weeds except Alopecurus were well controlled at 400 g/ha. Apart from wheat tolerance surprisingly good selectivity in maize was recorded at 100 g/ha with good control of Setaria, Abutilon, Cyperus, Ambrosia and Matricaria.

In post-emergence Example 7 displayed good cross spectrum control on both broadleaf weeds and grasses except Alopecurus with no observable crop tolerance. However, at 100 g/ha, good wheat tolerance was observed with excellent control of Setaria and all of the broadleaf weeds including *Galium aparine*.

TABLE 6

Pre- and post-emergence activity

| Example | Rate g/ha | Timing | Z E A M X | L X M A A | B T H P | A L O E N | P O H E | A T I M E Y | T E M G | L C H C V I | E C V I |
|---|---|---|---|---|---|---|---|---|---|---|---|

| 168 | 100  | PRE  | 1 | 0 | 9 | 9 | 7 | 9 | 9 | 2 | 6 | 9 |
|     | 25   |      | 0 | 0 | 9 | 6 | 3 | 8 | 3 | 0 | 1 | 5 |
|     | 12.5 |      | 0 | 0 | 9 | 3 | 0 | 8 | 1 | 0 | 0 | 2 |
| 169 | 400  | PRE  | 7 | 5 | 9 | 9 | 9 | 9 | 9 | 9 | 9 | 9 |
|     | 100  |      | 3 | 3 | 9 | 9 | 8 | 9 | 9 | 7 | 9 | 9 |
|     | 25   |      | 1 | 0 | 9 | 8 | 4 | 8 | 8 | 5 | 7 | 9 |
|     | 12.5 |      | 0 | 0 | 5 | 7 | 2 | 8 | 6 | 2 | 4 | 8 |
| 168 | 100  | POST | 3 | 9 | 9 | 9 | 9 | 9 | 9 | 3 | 8 | 9 |
|     | 25   |      | 1 | 6 | 9 | 9 | 9 | 9 | 7 | 1 | 2 | 7 |
|     | 12.5 |      | 0 | 5 | 9 | 9 | 9 | 8 | 7 | 0 | 0 | 6 |
| 169 | 400  | POST | 5 | 9 | 9 | 9 | 9 | 9 | 9 | 9 | 9 | 9 |
|     | 100  |      | 3 | 7 | 9 | 9 | 9 | 9 | 9 | 6 | 9 | 9 |
|     | 25   |      | 0 | 5 | 9 | 9 | 9 | 8 | 8 | 2 | 5 | 6 |

The indazole uracil of Example 168, showed good performance both in pre- and post-emergence. In pre-emergence all Alopecurus and four out of five broadleaf weeds were well controlled at 100 g/ha. Surprisingly good selectivity in maize and soy beans was recorded at 100 g/ha.

In post-emergence Example 168 displayed good cross spectrum control on both broadleaf weeds and grasses except Alopecurus and Echinochloa at 100 g/ha. At dose rate of 12.5 g/ha all broadleaf weeds were still well controlled.

The indole uracil of Example 169, showed excellent performance both in pre- and post-emergence. In pre-emergence all of the weeds except Alopecurus were well controlled at 100 g/ha. Surprisingly good selectivity in maize and soy beans was recorded at a dose rate of 25 g/ha with good control of Setaria, Abutilon, Galium, Matricaria and Stellaria.

In post-emergence Example 169 displayed good cross spectrum control on both broadleaf weeds and grasses at a dose rate of 100 g/ha. At the lowest dose rate of 12.5 g/ha excellent control of broadleaf weeds such as Abutilum, Galium, Ipomoea, Matricaria and Stellaria was recorded.

What is claimed is:

1. A 3-heterocycl-1-yluracil of formula (I)

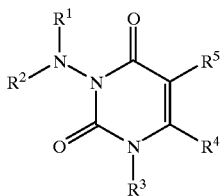

wherein
  $R^1$ and $R^2$ together with the interjacent nitrogen atom form an optionally benzo-condensed 5-membered heterocyclic ring, which may be substituted by up to 4 substituents selected from the group consisting of halogen, nitro, amino, hydroxy, cyano, $C_{1-6}$-alkyl, $C_{1-6}$-alkoxyimino-$C_{1-6}$-alkyl, alkenyloxyimino-$C_{1-6}$-alkyl, $C_{2-8}$-alkenyloxyimino-$C_{1-6}$-alkoxycarbonyl-$C_{1-6}$-alkyl, $C_{1-6}$-alkoxycarbonyl-$C_{1-6}$-alkoxyimino-alkyl, hydroxy-$C_{1-6}$-alkyl, $C_{1-6}$-alkoxy-$C_{1-6}$-alkyl, di-($C_{1-6}$-alkoxy)-$C_{1-6}$-alkyl, di-(alkylthio)-alkyl, $C_{1-6}$-alkylsulfonylamino-$C_{1-6}$-alkyl, halo-$C_{1-6}$-alkylsulfonylamino-$C_{1-6}$ alkyl, ($C_{-1-6}$ alkyl)n amino-$C_{1-6}$-alkyl, ($C_{1-6}$-alkylcarbonyloxy)$_z$-$C_{1-6}$-alkyl, halo-$C_{1-6}$-alkyl, cyano-$C_{1-6}$-alkyl, cyano-$C_{2-8}$-alkenyl formyl, $C_{1-6}$-alkylcarbonyl, or $ZR^8$,
  wherein
    Z is O, $NR^9$ or $S(O)_r$ or a single bond;
    $R^8$ is —$(R^{10})_s$—$CWR^{11}$, —$(R^{10})_s$—$SO_2R^{11}$, $C_{1-6}$-alkyl, halo-$C_{1-6}$-alkyl, hydroxy-$C_{1-6}$-alkyl, phenyl-$C_{1-6}$-alkyl, cyano-$C_{1-6}$-alkyl, $C_{1-6}$-alkanoxyoxy-$C_{1-6}$-alkyl, $C_{1-6}$-alkoxy-$C_{1-6}$-alkyl, di ($C_{1-6}$-alkoxy)-$C_{1-6}$-alkyl $C_{3-8}$-cycolalkyl, $C_{2-8}$-alkenyl, or $C_{2-8}$-alkynyl;
    $R^9$ is hydrogen, $C_{1-6}$-alkyl, $C_{2-8}$-alkenyl, $C_{2-8}$-alkynyl, formyl, amino or $C_{1-6}$-alkylcarbonyl;
    $R^{10}$ is $NR^{12}$, $C_{1-4}$-alkylidene or $C_{2-4}$ alkenylidene;
    $R^{11}$ is $C_{1-6}$-alkyl, halo-$C_{1-6}$-alkyl, halo-$C_{1-6}$-alkoxy, hydrogen, hydroxy, $C_{1-6}$-alkoxy, $C_{1-6}$-alkoxy-$C_{1-6}$-alkyl, $C_{1-6}$-alkoxy-$C_{1-6}$-alkoxy, $C_{1-6}$-alkoxy-$C_{1-6}$-alkylamino, di-$C_{1-6}$-alkoxy-$C_{1-6}$-alkylamino, phenyl, phenoxy, $C_{3-8}$-cycolalkyl, $C_{3-8}$-cycolalkoxy, phenyl-$C_{1-6}$-alkyl, $C_{1-6}$-alkoxycarbonyl, hydroxycarboxyl, $C_{1-6}$-alkoxycarbonyl-$C_{1-6}$-alkyl, $C_{1-6}$-alkoxycarbonyl-$C_{1-6}$-alkoxy, hydroxycarbonyl-$C_{1-6}$alkyl, hydroxycarbonyl-$C_{1-6}$alkoxy, ($C_{1-6}$-alkyl)$_r$ amino, ($C_{3-8}$-cycloalkyl)$_r$ amino, N-$C_{3-8}$-cycloalkyl-N-($C_{1-6}$-alkyl)$_s$ amino, ($C_{1-6}$-alkyl)$_r$ hydrazino, $C_{1-6}$-alkoxycarbonyl-$C_{1-6}$-alkylamino, hydroxy-$C_{1-6}$-alkylamino, ($C_{1-6}$-alkyl)$_r$ amino-$C_{1-6}$-alkylamino, ($C_{1-6}$-alkyl)$_r$ aminocarbonyl-$C_{1-6}$-alkylamino, hydroxycarbonyl-$C_{1-6}$-alkylamino, $C_{1-6}$-alkylsulfonylamino, phenylsulfonylamino, $C_{1-6}$-alkanoylaimino-$C_{1-6}$-alkylamino, N-$C_{1-6}$-alkoxy-N-($C_{1-6}$-alkyl), amino, N-hydroxy-N-($C_{1-6}$-alkyl)$_s$ amino, cyano-$C_{1-6}$-alkyl-amino, ($C_{2-8}$-alkenyl)$_r$ amino, $C_{1-6}$-alkoxy-$C_{1-6}$-alkylamino, ($C_{2-8}$-alkynyl)$_r$ amino, $C_{2-8}$-alkenyloxy, $C_{2-8}$-alkynyloxy, or semicarbazido;
    $R^{12}$ is hydrogen, $C_{1-6}$-alkyl, $C_{2-8}$-alkenyl, $C_{2-8}$-alkynyl, formyl, $C_{1-6}$-alkylsulfonyl, $C_{1-6}$-alkylcarbonyloxy or $C_{1-6}$-alkylcarbonyl;
    r represents an integer from 0 to 2;
    s represents 0 or 1;
    z represents 1 or 2;
  $R^3$ represents an amino, hydroxy, alkyl or alkoxy group;
  $R^4$ represents a halogen atom, or a formyl, a hydroxyiminomethyl, a cyano, a carboxy, an alkoxycarbonyl, a carbamoyl, a thiocarbamoyl, an alkyl, an alkoxy, an alkylthio, a haloalkyl, a haloalkoxy or a haloalkylthio group,
  $R^5$ represents a hydrogen or halogen atom, or an alkyl group; or an agriculturally acceptable salt or N-oxide thereof.

2. A 3-heterocycl-1-yluracil as claimed in claim 1, wherein
  $R^3$ represents a methyl group;
  $R^4$ represents a halogen atom, or a cyano, a $C_{1-4}$ fluoroalkyl, a $C_{1-4}$ fluoroalkoxy or a $C_{1-4}$ fluoroalkylthio group;
  $R^5$ represents a hydrogen atom.

3. A 3-heterocycl-1-yluracil as claimed in claim 1, wherein
  $NR^1R^2$ represents a group selected from the formulae (1) and (2)

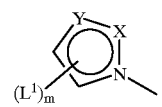

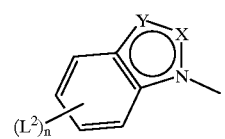

wherein
  X represents N or $CR^6$;
  Y represents N or $CR^7$;
  $R^6$ represents a hydrogen or halogen atom, or a formyl, a nitro, a alkoxyiminoalkyl, a cyano, a carboxy, an amino, an alkylamino, an alkoxycarbonyl, a carbamoyl, a thiocarbamoyl an alkyl or an alkoxy group,
  $R^7$ represents a hydrogen or halogen atom or an alkyl group;
  $L^1$ and $L^2$ each independently represent hydrogen, halogen, nitro, amino, hydroxy, cyano, $C_{1-6}$-alkyl, $C_{1-6}$-alkoxyimino-$C_{1-6}$-alkyl, alkenyloxyimino-$C_{1-6}$-alkyl, $C_{2-8}$-alkenyloxyimino-$C_{1-6}$-alkoxycarbonyl-$C_{1-6}$-alkyl, $C_{1-6}$-alkoxycarbonyl-$C_{1-6}$-alkoxyimino-alkyl, hydroxy-$C_{1-6}$-alkyl, $C_{1-6}$-alkoxy-$C_{16}$-alkyl, di-($C_{1-6}$-alkoxy)-$C_{1-6}$-alkyl, di-(alkylthio)-alkyl, $C_{1-6}$-alkylsulfonylamino-$C_{1-6}$-alkyl; halo-$C_{1-6}$-alkylsulfonylamino-$C_{1-6}$-alkyl, ($C_{1-6}$-alkyl), amino-$C_{1-6}$-alkyl, ($C_{1-6}$-alkylcarbonyloxy)$_z$-$C_{1-6}$-alkyl, halo-$C_{1-6}$-alkyl, cyano-$C_{1-6}$-alkyl, cyano-$C_{2-8}$-alkenyl, formyl, $C_{1-6}$-alkylcarbonyl; or
  $ZR^8$ wherein Z is O, $NR^9$ or $S(O)_r$ or a single bond;
  $R^8$ is —$(R^{10})_s$—$CWR^{11}$; —$(R^{11})_s$—$SO_2R^{11}$, $C_{1-6}$-alkyl, halo $C_{1-6}$-alkyl, hydroxy $C_{1-6}$phenyl $C_{1-6}$-alkyl, cyano $C_{1-6}$-alkyl, $C_{1-6}$-alkanoyloxy $C_{1-6}$-alkyl, $C_{1-6}$-alkoxy $C_{1-6}$-alkyl, $C_{3-8}$-cycloalkyl, $C_{2-8}$-alkenyl, di-($C_{1-6}$-alkoxy)-$C_{1-6}$-alkyl or $C_{2-8}$-alkynyl;
  $R^9$ is hydrogen, $C_{1-6}$-alkyl, $C_{2-8}$-alkenyl, $C_{2-8}$-alkynyl, amino, formyl or $C_{1-6}$-alkylcarbonyl;
  $R^{10}$ is $NR^{12}$, $C_{1-4}$-alkylidene or $C_{2-4}$-alkenylidene;

$R^{11}$ is $C_{1-6}$-alkyl, halo $C_{1-6}$-alkyl, halo $C_{1-6}$-alkoxy, hydrogen, hydroxy, $C_{1-6}$-alkoxy, $C_{1-6}$-alkoxy $C_{1-6}$-alkyl, $C_{1-6}$-alkoxy $C_{1-6}$-alkoxy, $C_{1-6}$-alkoxy $C_{1-6}$-alkylamino, di $C_{1-6}$-alkoxy $C_{1-6}$-alkylamino, phenyl, phenoxy, $C_{3-8}$-cycolalkyl, $C_{3-8}$-cycloalkoxy, phenyl-$C_{1-6}$-alkyl, $C_{1-6}$-alkoxycarbonyl, hydroxycarboxyl, $C_{1-6}$-alkoxycarbonyl $C_{1-6}$-alkyl, $C_{1-6}$-alkoxycarbonyl $C_{1-6}$-alkoxy, hydroxycarbonyl-$C_{1-6}$-alkyl, hydroxycarbonyl $C_{1-6}$-alkoxy, $(C_{1-6}$-alkyl$)_r$ amino, $(C_{3-8}$-cycloalkyl$)_r$ amino, N-$C_{3-8}$-cycloalkyl-N-$(C_{1-6}$-alkyl), amino, $(C_{1-6}$-alkyl$)_r$ hydrazino, $C_{1-6}$-alkoxycarbonyl-$C_{1-6}$-alkylamino, hydroxy $C_{1-6}$-alkylamino, $(C_{1-6}$-alkyl$)_r$ amino $C_{1-6}$-alkylamino, $(C_{1-6}$-alkyl$)_r$ aminocarbonyl-$C_{1-6}$-alkylamino, hydroxycarbonyl-$C_{1-6}$-alkylamino, $C_{1-6}$-alkylsulfonylamino, phenylsulfonylamino, $C_{1-6}$-alkanoylamino $C_{1-6}$-alkylamino, N-$C_{1-6}$-alkoxy-N-$(C_{1-6}$-alkyl$)_s$ amino, N-hydroxy-N-$(C_{1-6}$-alkyl$)_s$ amino, cyano $C_{1-6}$-alkyl-amino, $(C_{2-8}$-alkenyl), amino, $C_{1-6}$-alkoxy $C_{1-6}$-alkylamino; $(C_{2-8}$-alkynyl$)_r$ amino, $C_{2-8}$-alkenyloxy, $C_{2-8}$-alkynyloxy, or semicarbazido;

$R^{12}$ is hydrogen, $C_{1-6}$-alkyl, $C_{2-8}$-alkenyl, $C_{2-8}$-alkynyl, formyl, $C_{1-6}$-alkylcarbonyl, $C_{1-6}$-alkylcarbonyloxy, or $C_{1-6}$-alkylsulfonyl;

m represents 1 or 2;

n represents an integer from 1 to 4;

r represents an integer from 0 to 2;

s represents 0 or 1; and represents 1 or 2.

4. A 3heterocycl-1-yluracil of the formula IA

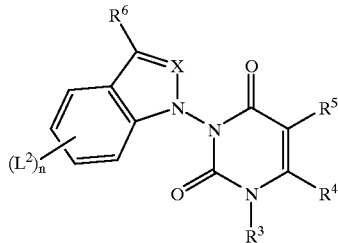

(IA)

wherein $R_3$ represents an alkyl group, $R_4$ represents a halogen atom, or a formyl, a hydoxyiminomethyl, a cyano, a carboxy, an alkoxycarbonyl, a carbamoyl, a thiocarbamoyl, an alkyl, an alkoxy, an alkylthio, a haloalkyl, a haloalkoxy or a haloalkylthio group;

$R_5$ represents a hydrogen atom;

X represents N or CR$^6$;

$R^6$ represents a hydrogen or halogen atom, or a formyl, a nitro, a alkoxyiminoalkyl, a cyano, a carboxy, an amino, an alkylamino, an alkoxycarbonyl, a carbamoyl, a thiocarbamoyl, an alkyl or an alkoxy group;

$L^2$ represents hydrogen, halogen, nitro, amino, hydroxy, cyano, $C_{1-6}$-alkyl, $C_{1-6}$-alkoxyimino-$C_{1-6}$-alkyl, alkenyloxyimino-$C_{1-6}$-alkyl, $C_{2-8}$alkenyloxyimino-$C_{1-6}$-alkoxyimino-alkyl, $C_{1-6}$-alkoxycarbonyl-$C_{1-6}$-alkoxyimino-alkyl, hydroxy-$C_{1-6}$-alkyl, $C_{1-6}$-alkoxy-$C_{1-6}$-alkyl, di-$(C_{1-6}$-alkoxy)-$C_{1-6}$-alkyl, di-(alkylthio)-alkyl, $C_{1-6}$-alkylsulfonylamino-$C_{1-6}$-alkyl, halo-$C_{1-6}$-alkylsulfonylamino-$C_{1-6}$-alkyl, $(C_{1-6}$-alkyl)n amino-$C_{1-6}$-alkyl, $(C_{1-6}$-alkylcarbonyloxy$)_z$—$C_{1-6}$-alkyl, halo-$C_{1-6}$-alkyl, cyano —$C_{1-6}$-alkyl, cyano-$C_{2-8}$-alkenyl formyl, $C_{1-6}$-alkylcarbonyl;

$ZR^8$ wherein Z is O, NR$^9$ or S(O)$_r$ or a single bond;

$R^8$ is —$(R^{10})_s$—CWR$^{11}$, —$(R^{11})_s$—SO$_2$R$^{11}$, $C_{1-6}$-alkyl, halo-$C_{1-6}$-alkyl, hydroxy-$C_{1-6}$-alkyl, phenyl-$C_{1-6}$-alkyl, cyano-$C_{1-6}$-alkyl, $C_{1-6}$-alkanoyloxy-$C_{1-6}$-alkyl, $C_{1-6}$-alkoxy-$C_{1-6}$-alkyl, di-$(C_{1-6}$-alkoxy)-$C_{1-6}$-alkyl $C_{3-8}$-cycolalkyl, $C_{2-8}$-alkenyl, or $C_{2-8}$-alkynyl; $R^9$ is hydrogen, $C_{1-6}$-alkyl, $C_{2-8}$-alkenyl, $C_{2-8}$-alkynyl, formyl, amino or $C_{1-6}$-alkylcarbonyl;

$R^{10}$ is NR$^{12}$, $C_{1-4}$ alkylidene or $C_{2-4}$ alkenylidene;

$R^{11}$ is $C_{1-6}$-alkyl, halo-$C_{1-6}$-alkyl, halo-$C_{1-6}$-alkoxy, hydrogen, hydroxy, $C_{1-6}$-alkoxy, $C_{1-6}$-alkoxy-$C_{1-6}$-alkyl, $C_{1-6}$-alkoxy-$C_{1-6}$-alkoxy, C-$_{1-6}$-alkoxy-$C_{1-6}$-alkylamino, di-$C_{1-6}$ alkoxy-$C_{1-6}$-alkylamino, phenyl, phenoxy, $C_{3-8}$-cycolalkyl, $C_{3-8}$-cycolalkoxy, phenyl-$C_{1-6}$-alkyl, $C_{1-6}$-alkoxycarbonyl, hydroxycarboxyl, $C_{1-6}$-alkoxycarbonyl-$C_{1-6}$-alkyl, $C_{1-6}$-alkoxycarbonyl-$C_{1-6}$-alkoxy, hydroxycarbonyl-$C_{1-6}$ alkyl, hydroxycarbonyl-$C_{1-6}$ alkoxy, $(C_{1-6}$-alkyl$)_r$ amino, $(C_{3-8}$-cycloalkyl$)_r$ amino, N-$C_{3-8}$-cycloalkyl-N-$(C_{1-6}$-alkyl$)_s$ amino, $(C_{1-6}$-alkyl$)_r$ hydrazino, $C_{1-6}$-alkoxycarbonyl-$C_{1-6}$-alkylamino, hydroxy-$C_{1-6}$-alkylamino, $(C_{1-6}$-alkyl$)_r$ amino-$C_{1-6}$-alkylamino, $(C_{1-6}$-alkyl$)_r$ aminocarbonyl-$C_{1-6}$-alkylamino, hydroxycarbonyl-$C_{1-6}$-alkylamino, $C_{1-6}$-alkylsulfonylamino, phenylsulfonylamino, $C_{1-6}$-alkanoylamino-$C_{1-6}$-alkylamino, N-$C_{1-6}$-alkoxy-N-$(C_{1-6}$-alkyl), amino, N-hydroxy-N-$(C_{1-6}$-alkyl$)_s$ amino, cyano-$C_{1-6}$-alkyl-amino, $(C_{2-8}$-alkenyl$)_r$ amino, $C_{1-6}$-alkoxy-$C_{1-6}$-alkylamino, $(C_{2-8}$-alkynyl$)_r$ amino, $C_{2-8}$-alkenyloxy, $C_{2-8}$-alkynyloxy, or semicarbazido;

$R^{12}$ is hydrogen, $C_{1-6}$-alkyl, $C_{2-8}$-alkenyl, $C_{2-8}$-alkynyl, formyl, $C_{1-6}$-alkylsulfonyl, $C_{1-6}$-alkylcarbonyloxy or $C_{1-6}$-alkylcarbonyl;

M or Q is $C_{1-6}$-alkoxy, $C_{1-6}$-alkyl, $(C_{1-6}$-alkyl$)_r$ amino, hydroxy, hydrogen, $C_{2-6}$-alkenyloxy, $(C_{2-8}$-alkenyl$)_r$ amino, $C_{2-8}$-alkynyloxy, or $(C_{2-8}$-alkynyl), amino.

5. A 3-heterocycl-1-yluracil as claimed in claim 4, wherein $R^3$ represents a methyl group;

$R^4$ represents a halogen atom, or a cyano, a $C_{1-4}$ fluoroalkyl, a $C_{1-4}$ fluoroalkoxy or a $C_{1-4}$ fluoroalkylthio group, and $R^5$ represents a hydrogen atom.

6. A 3-heterocycl-1-yluracil of formula 1A as claimed in claim 4, wherein X represents CH or N.

7. A 3-heterocycl-1-yluracil according to claim 4, wherein $R^4$ represents a trifluoromethyl group.

8. A 3-heterocycl-1-yluracil according to claim 4 selected from the group consisting of 1-methyl-3-(6-nitro-indol-1-yl)-6-trifluoromethyl-uracil, of 1-methyl-3-(5-nitro-indol-1-yl)-6-trifluoromethyl-uracil, 1-methyl-3-(6-methoxy-indol-1-yl)-6-trifluoromethyl-uracil, 1-methyl-3-(6-nitro-indazol-1-yl)-6-trifluoromethyl-uracil, 1-methyl-3-(5-nitro-indazol-1-yl)-6-trifluoromethyl-uracil and 1-methyl-3-(6-methoxy-indazol-1-yl)-6-trifluoromethyl-uracil.

9. A process for the preparation of a compound of formula IA as claimed in claim 4, which comprises reacting an aminoalkenoate of formula II, (II)

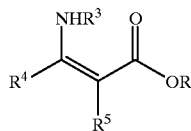

in which $R^3$ through $R^5$ have the meaning given in claim 4, and R represents an alkyl, aryl or aralkyl group, with a heterocycl-1-ylcarbamate of formula III (III)

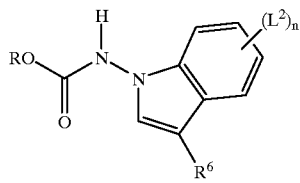

in which $R^6$, X, $L^2$ and n have the meaning given I claim 4, and R represents an alkyl, aryl or aralkyl group.

10. A process for the preparation of a compound of formula IA as claimed in claim 4 wherein $R^3$ represents a hydrogen atom or an alkyl group, which comprises the steps of (a) reacting an oxazine of formula IV, (IV)

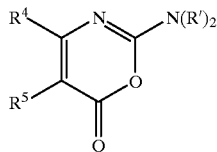

in which $R^4$ and $R^5$ have the meaning given in claim 4, and R' represents a hydrogen atom or an alkyl, aryl or aralkyl group, with a heterocycl-1-ylamine of formula V (V)

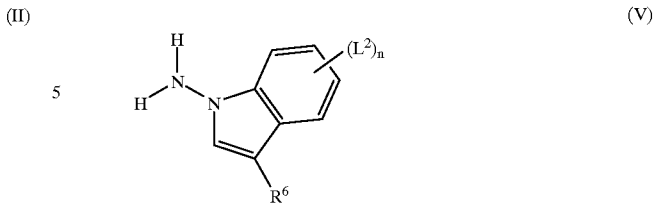

in which $R^1$ and $R^2$ have the meaning given in claim 4 and (b) optionally treating the resulting 3-heterocycl-1-yluracil of formula (IA1)

(IA$_1$)

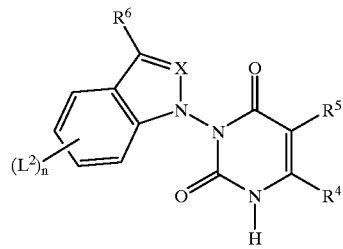

with an alkylating agent of formula VI $R^3$—LG  (VI)

in which $R^3$ has the meaning given in claim 4, and

LG represents a suitable leaving group.

11. A herbicidal composition comprising an effective amount of one or more compounds of formula I, as claimed in claim 4, together with a carrier.

12. A composition as claimed in claim 11, comprising at least two carriers, at least one of which is a surface-active agent.

13. A method of combating undesired plant growth at a locus, comprising application to the locus of an effective amount of a compound of formula I, as claimed in claim 4.

\* \* \* \* \*

UNITED STATES PATENT AND TRADEMARK OFFICE
CERTIFICATE OF CORRECTION

PATENT NO.    : 6,376,426 B1
DATED         : April 23, 2002
INVENTOR(S)   : Scheiblich et al.

It is certified that error appears in the above-identified patent and that said Letters Patent is hereby corrected as shown below:

Column 25,
Lines 56 and 57, "$C_{1-6}$-alkanoylaimino-$C_{1-6}$-alkylamino, N-$C_{1-6}$-alkoxy-N-($C_{1-6}$-alkyl), amino" should be -- $C_{1-6}$-alkanoylamino-$C_{1-6}$-alkylamino, N-$C_{1-6}$-alkoxy-N-($C_{1-6}$-alkyl)$_s$ amino --.

Column 26,
Line 51, "$C_{16}$-alkyl" should be -- $C_{1-6}$-alkyl --.
Line 54, "($C_{1-6}$-alkyl)," should be -- ($C_{1-6}$-alkyl)$_n$ --.
Line 60, "-($R^{11}$)$_s$," should be -- -($R^{10}$)$_s$ --.
Line 61, "hydroxy $C_{1-6}$phenyl" should be -- hydroxy $C_{1-6}$-alkyl, phenyl --.

Column 27,
Line 10, "($C_{1-6}$-)alkyl," should be -- ($C_{1-6}$-)alkyl$_s$ --.

Column 28,
Line 31, "($C_{1-6}$-)alkyl," should be -- ($C_{1-6}$-)alkyl$_s$ --.
Line 40, "$C_{2-6}$-alkenyloxy" should be -- $C_{2-8}$-alkenyloxy --.
Line 41, "($C_{2-8}$-alkynyl)," should be -- ($C_{2-8}$-alkynyl)$_r$ --.

Signed and Sealed this

Sixth Day of May, 2003

JAMES E. ROGAN
*Director of the United States Patent and Trademark Office*